(12) United States Patent
Godbole et al.

(10) Patent No.: US 7,250,527 B2
(45) Date of Patent: Jul. 31, 2007

(54) PROCESS FOR RECOVERING ACRYLONITRILE OR METHACRYLONITRILE

(75) Inventors: Sanjay P. Godbole, Solon, OH (US); Mark C. Cesa, Wheaton, IL (US)

(73) Assignee: Ineos USA LLC, Lisle, IL (US)

( * ) Notice: Subject to any disclaimer, the term of this patent is extended or adjusted under 35 U.S.C. 154(b) by 264 days.

(21) Appl. No.: 10/736,387

(22) Filed: Dec. 15, 2003

(65) Prior Publication Data

US 2004/0181086 A1 Sep. 16, 2004

Related U.S. Application Data

(60) Provisional application No. 60/437,836, filed on Jan. 3, 2003.

(51) Int. Cl.
*C07C 255/08* (2006.01)
(52) U.S. Cl. ..................................................... 558/463
(58) Field of Classification Search ................. 558/463
See application file for complete search history.

(56) References Cited

U.S. PATENT DOCUMENTS

| | | | |
|---|---|---|---|
| 2,987,451 A | 6/1961 | Sennewald et al. | 202/57 |
| 3,255,233 A | 6/1966 | Kunze et al. | 260/465.3 |
| 3,459,639 A | 8/1969 | Borrel et al. | 203/37 |
| 3,468,624 A | 9/1969 | Miller et al. | 23/119 |
| 3,896,007 A | 7/1975 | Rescalli et al. | 203/33 |
| 4,059,492 A | 11/1977 | Hausweiler et al. | 203/11 |
| 5,606,094 A | 2/1997 | Roof et al. | 558/463 |
| 6,074,532 A | 6/2000 | Patel et al. | 203/6 |
| 6,793,776 B2 * | 9/2004 | Godbole | 203/6 |

FOREIGN PATENT DOCUMENTS

| | | |
|---|---|---|
| GB | 0821958 | 10/1959 |
| GB | 1431511 A | 4/1976 |
| GB | 0714385 | 8/1994 |

OTHER PUBLICATIONS

Abstract JP 71013726B; Derwent; Acrylonitrile Separation From Propylene-Ammoxidation Mixture.

* cited by examiner

*Primary Examiner*—Johann Richter
*Assistant Examiner*—Ebenezer Sackey
(74) *Attorney, Agent, or Firm*—David P. Yusko

(57) ABSTRACT

A process for the recovery of acrylonitrile or methacrylonitrile from an aqueous solution comprising subjecting the said solution to a water extractive distillation by feeding the solution to a distillation column and performing said extractive distillation and using solvent water introduced at the top of said column, removing a first overhead vapor stream of acrylonitrile or methacrylonitrile with some water from the top of the column, and a first liquid stream containing water and impurities from the bottom of the column, the contents of said column maintained at a substantially neutral pH by adding a sufficient amount of at least one alkaline compound selected from ammonium carbonate, ammonium bicarbonate, ammonium carbamate, and alkylene diamines to the overhead decanter and/or to the solvent water.

7 Claims, No Drawings

PROCESS FOR RECOVERING ACRYLONITRILE OR METHACRYLONITRILE

This application claims the benefit of U.S. Provisional Application No. 60/437,836, having a filing date of Jan. 3, 2003.

BACKGROUND OF THE INVENTION

This invention is directed to an improved process for the recovery of nitrile monomer from the reactor effluent from a hydrocarbon ammoxidation reactor. More particularly, the invention is directed to an improved process for the recovery of nitrile monomer contained in the effluent stream from the ammoxidation of propylene, propane, isobutane or isobutylene in the production of acrylonitrile or methacrylonitrile.

The processes widely used in commercial practice for recovering the products of hydrocarbon ammoxidation generally comprise the steps of: a) contacting the effluent from an ammoxidation reactor in a quench tower with an aqueous quench liquid to cool the gaseous effluent; b) contacting the quenched effluent with water in an absorber, forming an aqueous solution comprising the ammoxidation products; c) subjecting said aqueous solution to extractive distillation with water in the recovery column to separate the crude monomer as an overhead vapor stream and collect water soluble, less volatile contaminants in a liquid waste stream from the bottom of the column; and d) condensing an overhead vapor stream to form an organic phase comprising nitrile monomer and an aqueous phase, and decanting the organic phase containing crude monomer. Further purification of the nitrile monomer may be accomplished by passing said organic phase to a second distillation column to remove at least some impurities from the crude nitrile monomer, and further distilling the partially purified nitrile in a third distillation column to obtain the purified acrylonitrile or methacrylonitrile.

Processes for recovery and purification of acrylonitrile and methacrylonitrile are well known and widely described in the art, for example, in U.S. Pat. Nos. 6,107,509, 4,234,510, 3,885,928, 3,459,639, 3,352,764, and 3,198,750. The entire disclosure of each of said patents is incorporated herein by reference.

Hydrocarbon ammoxidation, particularly of alkanes, is typically conducted using substantial excesses of ammonia. Ammonia that is not consumed in the ammoxidation exits the reactor in the effluent, together with nitrile monomer and reaction by-products including hydrocyanic acid, cyanoalkane and the corresponding aldehyde and the like. The by-products react with nitrile monomer in the presence of unreacted ammonia, or with one another. It is therefore necessary to separate the ammonia from the effluent stream immediately after the stream exits the ammoxidation reactor. Conventionally, the unreacted ammonia is removed in the form of a salt as a part of the quench operation, step a, by including sufficient acid, for example, sulfuric acid, in the aqueous quench liquid to neutralize and capture the excess ammonia. Depending upon several process factors including the ability to accurately meter and control the addition of the several reaction components and the reaction parameters, substantially all of the excess ammonia will be captured in the quench step.

The aqueous solution obtained from the absorber in the subsequent absorption step (step b) will comprise the water soluble components of the effluent including nitrile monomer, the corresponding coproducts including alkylnitrile and hydrocyanic acid, together with minor amounts of contaminants. For example, in an acrylonitrile process, the solution will include acrylonitrile, acetonitrile and HCN, together with a minor amounts of acrolein and other carbonyl compounds, residual ammonia, cyanohydrins and other contaminants. The pH will vary, depending in part upon the relative levels of HCN and residual ammonia.

Acrylonitrile and valuable coproducts including acetonitrile are separated in the recovery column. The separation is greatly affected by the pH of the system, which will preferably be maintained in the range of from about 5.5 to about 7.5, more preferably from about 6 to about 7. Within the preferred pH range, acrolein and other carbonyl contaminants react with water and HCN, forming high molecular weight, water soluble products that remain with the aqueous phase. Maintaining the system pH in the preferred range will also neutralize other volatile contaminants including nitrogen oxides, removing them from the product stream. A more alkaline condition promotes formation of HCN trimers and polymers, and leads to loss of product through nitrile hydrolysis and polymerization of nitrile monomer. Side reactions form high molecular weight products that may be carried into the column and lead to fouling of the column. At a low pH, acrolein and other volatile contaminants may escape to the overhead and contaminate the product stream.

The recovery column may be maintained at a near neutral pH by monitoring the pH and adding an appropriate amount of an alkaline compound to the system as required. The addition may be made at any convenient point; typically, the addition will be to the aqueous phase in the overhead decanter and to the solvent water fed to the column.

A variety of water soluble caustic additives including alkali metal hydroxides such as potassium hydroxide and sodium hydroxide have been disclosed in the art for this use, as have ammonia, alkyl amines and the like. However, these additives tend to react with one or more of the products. Contacting the product stream with strong caustics may initiate polymerizations and other side reactions; to avoid these difficulties, the caustic will be well-diluted with water, further adding to the disposal problem. Ammonia and water soluble alkyl amines undergo cyanoethylation by the nitrile monomer, and amines may be sufficiently soluble in acrylonitrile to be carried into the product stream.

Salts of weak acids, for example, alkali metal and alkaline earth metal carbonates, bicarbonates, acetates, phosphates and the like have also been disclosed for this use, for example, in U.S. Pat. No. 3,896,740. These mildly alkaline compounds may be added directly to the column or to a process stream without causing significant product loss. The additive most commonly employed in commercial processes for this purpose is soda ash, in part because of its low cost and ready availability. The residual salts resulting from the neutralization accumulate in the still bottoms and are eventually purged from the process as wastewater. Where the neutralizing additive is soda ash or caustic soda, the wastewater will necessarily contain a high level of sodium salts.

Acrylonitrile plants generate a significant volume of wastewater containing organic compounds, ammonia, and inorganic salts. Methods for treating or disposing of these streams include thermal or catalytic incineration, biotreatment, wet oxidation and reduction, and deep welling. These disposal methods represent current general industry practice. Producers of acrylonitrile are, however, studying alternative methods of wastewater handling. Currently, much of the wastewater generated by acrylonitrile plants in the United States is disposed of by the deep welling of streams with low levels of contaminants and the incineration of streams with higher levels of impurities.

Incineration of aqueous wastes containing high levels of sodium gives rise to serious corrosion problems, including erosion of the incinerator furnace refractory liner. Periodic shut-downs of the plant are needed to allow repair of the incinerator and replacement of the refractory, substantially adding to operating costs. Substantially reducing the level of sodium in effluent wastewater, thereby reducing damage to the incinerator and increasing the time between shutdowns, would thus provide a significant economic benefit.

SUMMARY OF THE INVENTION

The present invention is directed to an improved process for the recovery of acrylonitrile or methacrylonitrile from an aqueous product stream comprising nitrile monomer and coproducts produced by an ammoxidation process. More particularly, the invention is directed to an improved extractive distillation process for the recovery of acrylonitrile or methacrylonitrile wherein the pH of the recovery column is maintained near neutral with an additive selected from ammonium carbonate, ammonium carbamate, mixtures comprising ammonium carbonate and ammonium carbamate, and alkylene diamines.

More fully described, the nitrile monomer recovery process will comprise: contacting an effluent containing acrylonitrile or methacrylonitrile from an ammoxidation reactor with an aqueous quench liquid in a first column (quench); contacting the gaseous quench effluent with water in a second column (absorber), thereby forming an aqueous solution comprising nitrile monomer and coproducts; and subjecting said aqueous solution to a water extractive distillation in a distillation column (recovery) while maintaining the pH of said distillation column in the range of from about 5.5 to about 7.5, preferably in the range of from about 6 to about 7, by adding at least one alkaline compound selected from ammonium carbonate, ammonium bicarbonate, ammonium carbamate, and alkylene diamines to the system. Typically, the absorber column and recovery column are maintained at a pressure in the range of from 0 to 20 psig.

Further purification may be accomplished by passing the overhead vapor stream of nitrile to a second distillation column (heads column) to remove at least some of the impurities from the crude nitrile, and further distilling the partially purified nitrile in a third distillation column (product column) to obtain product acrylonitrile or methacrylonitrile.

In a preferred embodiment of the present invention, the reactor effluent is obtained from the reaction zone of a catalyzed ammoxidation of propane or propylene, ammonia and oxygen in the production of acrylonitrile.

In another preferred embodiment, the alkaline compound is selected from ammonium carbonate, ammonium bicarbonate, ammonium carbamate and mixtures thereof.

In another preferred embodiment, the alkaline compound is generated in situ by adding ammonia and carbon dioxide to at least one of the solvent water employed in the extractive distillation and the aqueous phase of the overhead decanter.

DETAILED DESCRIPTION OF THE INVENTION

In the improved process of this invention, an aqueous solution comprising nitrile monomer and coproducts, for example the aqueous product stream from the adsorption column of an ammoxidation process, is fed to a distillation column and subjected to a water extractive distillation wherein solvent water is introduced at the top of said column. A first overhead vapor stream comprising nitrile monomer with some water will be removed from the top of the column and condensed to an overhead decanter, and a first liquid stream containing water and water soluble coproducts and impurities will be taken from the bottom of said column.

Typically, the aqueous product stream from the adsorption column will comprise acrylonitrile or methacrylonitrile together with reaction byproducts including acrolein, acetonitrile (or methyl-substituted analogs), HCN, and ammonium salts, typically ammonium sulfates. Various contaminants such as cyanohydrins, nitrogen oxides and the like arising from side reactions may also be present. The pH will vary, depending in part upon several process factors, including the ability to accurately meter the addition of the several reaction components and to control the ammoxidation reaction parameters. Excursions in the process control may create larger-than-anticipated deviations in the ammonia content of the reactor effluent. If not completely removed in the quench step, ammonia may be carried into the recovery column, alkalizing the column and the overhead decanter.

The distillation column is maintained at a near-neutral pH in the range of from about 5.5 to about 7.5, more preferably in the range of from about 6 to about 7, to minimize loss of product. The art discloses the use of caustic soda and a variety of other caustics for neutralizing excess acidity in the column. Where ammonia is present in the process stream, alkalizing the column and requiring the addition of an acidic compound to adjust the pH, the art further discloses the use of acetic acid and the like as additives.

In the improved process of this invention, maintaining the distillation column at a near neutral pH will be accomplished by adding an alkaline compound selected from the group consisting of ammonium carbonate, ammonium carbamate, alkylene diamines, and mixtures thereof, to the water being recovered and cycled to the column as solvent water.

The acidity of a process stream from the quench column, and thereby the acidity of the aqueous solution can vary widely with time. Adding ammonium carbonate to the aqueous stream in the column will a carbonate/bicarbonate mixture. The buffering ability of ammonium carbonate/bicarbonate mixtures serves to maintain the pH near neutral, whether a deviation in the process stream causes an increase or a decrease in the acid components. Thus, ammonia present in the process stream may be absorbed by the ammonium bicarbonate to form ammonium carbonate, avoiding the need to provide for the use of an acid additive. Moreover, aqueous solutions of ammonium carbonate are only mildly alkaline; a modest excess of ammonium carbonate will be tolerated by the system without risk of product loss by alkalizing the column.

Ammonium carbonate and its anhydride, ammonium carbamate, are readily available from commercial sources, as is ammonium bicarbonate. The commercial grade of ammonium carbonate is said to be a double salt of ammonium bicarbonate and ammonium carbamate, $NH_4HCO_3 \cdot NH_2CO_2NH_4$. Alternatively, ammonium carbonates are conveniently prepared by contacting aqueous ammonia and carbon dioxide, preferably in an absorption apparatus, and controlling the exothermic process with appropriate cooling means.

Alkylene amines, for example, ethylene diamine, propylene diamine, hexamethylene diamine and the like, as well as cyclic analogs thereof, are also water soluble difunctional bases capable of forming buffered aqueous solutions. A wide variety of suitable diamines are readily available from commercial sources, and these may also be found useful, singly or in combination, to provide buffered systems for neutralizing the aqueous solution from the absorber. Both the alkylene diamine and the corresponding mono- and di-amminium salts that result on titrating with acidic components of the process stream are necessarily water soluble. Secondary and tertiary amines such as, for example, N,N'-dimethyl ethylene diamine, N,N,N'N'-tetramethyl ethylene diamine and the like, are less susceptible to being cyanoethylated, and thus may be preferred.

The amount of the alkaline compound added will be sufficient to maintain the pH of the recovery column near neutral. Diamines and ammonium carbonates may conveniently be added to the overhead decanter of the distilling column and to the solvent water. Alternatively, ammonium carbonate may be generated in situ by separately adding appropriate quantities of ammonia and carbon dioxide to the cycle water.

EXAMPLES

Seven samples of acidic column feed collected from the absorber column were neutralized by adding sufficient amounts of an alkaline additive to produce a pH of 7. The additives and the quantities used are summarized in the following Table 1.

A portion of each was allowed to stand at room temperature for 20 hrs. to determine the amount of pH drift. The results are summarized in Table 1.

Separate portions of each were treated with equal amounts of acetic acid. The change in pH for each is summarized in Table 1.

The cyanoethylation rate, relative to diethyl amine, was also determined for each additive. The results are summarized in Table 1.

TABLE 1

| Example | Additive | Relative moles | pH drift | Acetic acid pH shift | Rel. rate cyanoeth. |
|---|---|---|---|---|---|
| 1 | Ammonium carbonate | 2.08 | 0.06 | 0.37 | 0.040 |
| 2 | $H_2NCH_2CH_2NH_2$ | 1.22 | 0.08 | 0.38 | 1.75 |
| 3 | $(CH_3)_2NCH_2CH_2N(CH_3)_2$ | 1.33 | 0.06 | 0.37 | .003 |
| Comp. 1 | ammonia | 2.36 | 0.11 | 0.73 | 0.018 |
| Comp. 2 | diethyl amine | 2.76 | 0.41 | 1.23 | 1.00 |
| Comp. 3 | trimethyl amine | 2.79 | 0.22 | 0.85 | 0.003 |
| Comp. 4 | sodium carbonate | 1.00 | 0.07 | 0.45 | <0.003 |

Though twice the molar amount of ammonium carbonate, compared with sodium carbonate, is required to produce a pH of 7, the buffering ability of ammonium carbonate is greater, as reflected in the lower shift in pH with the addition of acetic acid.

Loss in acrylonitrile due to cyanoethylation will be seen to be acceptably low for ammonium carbonate and for N,N,N',N'-tetramethyl ethylene diamine. The cyanoethylation rate for ethylene diamine, a primary amine, is very much greater, causing an unacceptable loss in acrylonitrile.

The methods and process steps of the invention are described and illustrated in terms of particular embodiments in connection with the ammoxidation of hydrocarbons in the production of nitrile monomers. However, those skilled in the art will recognize that many alternatives, modifications and variations of the described methods may be found suitable for use in the practice of this invention. Such modifications and additions, as well as compositions, formulations and apparatus embodying them, are contemplated to lie within the scope of the invention, which is defined and set forth in the following claims.

U.S. Provisional Application 60/437,836 having a filing date of Jan. 3, 2003 is incorporated herein by reference.

We claim:

1. In a process for the manufacture of nitrile monomer selected from the group consisting of acrylonitrile and methacrylonitrile, said process comprising contacting a gaseous effluent comprising nitrile monomer from an ammoxidation reactor with an aqueous quench liquid in a first column; contacting the gaseous quench effluent from said first column with water in a second column, thereby forming an aqueous solution comprising nitrile monomer and coproducts; and subjecting said aqueous solution to a water extractive distillation in a recovery distillation column employing solvent water and collecting said nitrile monomer together with water in an overhead decanter wherein the pH of the contents of said distillation column is maintained in the range of from about 5.5 to about 7.5 by adding an alkaline compound, the improvement wherein said alkaline compound is selected from the group consisting of ammonium carbonate, ammonium bicarbonate, ammonium carbamate, alkylene diamine, and mixtures thereof.

2. The process of claim 1, the improvement wherein said pH is maintained in the range of from about 6 to about 7.

3. The process of claim 1, the improvement wherein said alkaline compound is ammonium carbonate.

4. The process of claim 1, the improvement wherein said alkaline compound is a mixture comprising ammonium bicarbonate and ammonium carbamate.

5. The process of claim 2, the improvement wherein said ammonium carbonate is generated in situ by adding ammonia and carbon dioxide to said solvent water.

6. The process of claim 1, the improvement wherein said alkaline compound is an alkylene diamine.

7. The process of claim 1, the improvement wherein said alkaline compound is an alkylene diamine selected from the group consisting of ethylene diamine and an N,N,N',N'-tetraalkyl ethylene diamine.

* * * * *